US006620797B2

United States Patent
Chowhan et al.

(10) Patent No.: US 6,620,797 B2
(45) Date of Patent: Sep. 16, 2003

(54) ARTIFICIAL TEAR COMPOSITION CONTAINING A COMBINATION OF THREE DEMULCENTS

(75) Inventors: Masood A. Chowhan, Arlington, TX (US); Huagang Chen, Irving, TX (US)

(73) Assignee: Alcon, Inc., Hunenberg (CH)

( * ) Notice: Subject to any disclaimer, the term of this patent is extended or adjusted under 35 U.S.C. 154(b) by 0 days.

(21) Appl. No.: 10/021,766

(22) Filed: Dec. 13, 2001

(65) Prior Publication Data

US 2002/0123482 A1 Sep. 5, 2002

Related U.S. Application Data

(60) Provisional application No. 60/257,567, filed on Dec. 21, 2000.

(51) Int. Cl.[7] ............................................... A01N 25/00
(52) U.S. Cl. ............................ 514/57; 514/54; 514/58; 514/59; 514/839; 514/912; 514/915; 536/102; 536/103; 536/123.1
(58) Field of Search ............................. 514/54, 58, 59, 514/839, 912, 915; 536/102, 103, 123.1

(56) References Cited

U.S. PATENT DOCUMENTS

| | | | | |
|---|---|---|---|---|
| 4,039,662 | A | 8/1977 | Hecht et al. ................. | 424/180 |
| 5,403,598 | A | 4/1995 | Beck et al. ................... | 424/717 |
| 5,741,817 | A | 4/1998 | Chowhan et al. ............ | 514/561 |
| 5,800,807 | A | * 9/1998 | Hu et al. ................... | 424/78.04 |
| 6,143,799 | A | 11/2000 | Chowhan et al. ............ | 514/839 |
| 6,153,568 | A | * 11/2000 | McCanna et al. ............ | 510/112 |
| 6,184,189 | B1 | * 2/2001 | Asgharian et al. .......... | 510/112 |

FOREIGN PATENT DOCUMENTS

| | | |
|---|---|---|
| WO | WO 92/00707 | 1/1992 |
| WO | WO 96/14829 | 5/1996 |
| WO | WO 98/32421 | 7/1998 |

OTHER PUBLICATIONS

United States Pharmacopoeia 24th Edition (2000), Section 51, pp. 1809–1811.
Physician' Desk Refernce for Ophthalmology; 27th Edition (1999), Medications for Dry Eye, p. 13.
Physician' Desk Reference for Ophthalmology, 27th Edition (1999), Bion® Tears, p. 211.
Physicians' Desk Reference for Ophthalmology, 27th Edition (1999), Tears Naturale® II and Tears Naturale Free®, p. 221.
Physicians' Desk Reference for Ophthalmology, 27th Edition (1999), Ocucoat® and Ocucoat PF®, p. 254.
Handbook of Non–Prescription Drugs, 9th Edition, (1990), pp. 596–597.
Handbook of Non–Prescription Drugs, 12th Edition, (2000), p. 487.
Martindale The Complete Drug Reference, 32nd Edition, (1999), Pharmaceutical Press; p. 1886.
Murube, J., Tratamiento Substitutivo Del Ojo Seco: Lagrimas Artificiales; Capitulo 39, pp. 1–19.
Ophthalmic Drug Facts, (1993), p. 88.

* cited by examiner

Primary Examiner—James O. Wilson
Assistant Examiner—Patrick Lewis
(74) Attorney, Agent, or Firm—Gregg C. Brown

(57) ABSTRACT

Improved artificial tear compositions are described. The compositions are preferably formulated as sterile, isotonic solutions. The solutions contain a unique combination of three demulcents. The solutions preferably also contain one or more electrolytes and may also contain a nonionic surfactant. The solutions provide ocular comfort and are particularly useful in patients that are experiencing mild to moderate dryness or other irritation of the cornea. The solutions may be packaged as either an unpreserved unit dose product or as a preserved multi-dose product. The multi-dose products contain a very mild antimicrobial preservative system, and consequently can be frequently applied to the eye with little risk of ocular irritation attributable to the preservative components.

5 Claims, No Drawings

US 6,620,797 B2

ARTIFICIAL TEAR COMPOSITION CONTAINING A COMBINATION OF THREE DEMULCENTS

CROSS-REFERENCE TO RELATED APPLICATION

The present application claims priority under 35 U.S.C. §1.119(e) based on U.S. patent application Ser. No. 60/257,567 filed on Dec. 21, 2000

BACKGROUND OF THE INVENTION

The present invention relates to the field of artificial tear formulations. More specifically, the invention is directed to an improved artificial tear formulation that provides an increased lubricating effect, an enhanced ability to wet the surface of the cornea, and a greater ability to promote the retention of moisture by the cornea.

The sensation of ocular discomfort commonly referred to as "dry eye" can be caused by various factors. The principal causative factors are: (i) inadequate tear production attributable to aging, medical procedures performed on the cornea (e.g., LASIK), or other conditions; (ii) ocular irritants (e.g., dust, smoke, wind, sun or low humidity); and (iii) eyestrain attributable to extended viewing of computer monitors or other circumstances. Various products for alleviating the symptoms of dry eye have been proposed and several such products have been marketed.

One of the earliest and most successful artificial tear solutions is described in U.S. Pat. No. 4,039,662 (Hecht, et al.). This solution has been marketed for many years as TEARS NATURALE® Lubricant Eye Drops (Alcon Laboratories, Inc., Fort Worth, Tex.). The solution described and claimed in the Hecht, et al. '662 patent and the corresponding commercial product are based on the use of a unique combination of hydroxypropyl metbylcellulose, Dextran 70 and benzalkonium chloride. In a later version of this product, which is marketed under the name TEARS NATURALE® II (Alcon Laboratories, Inc.), the benzalkonium chloride was replaced by polyquaternium-1, which is a polymeric antimicrobial agent/preservative.

Both of the above-cited products offer relief from the symptoms collectively referred to herein as "dry eye" and both have been commercially successful. However, a need exists for improved artificial tear products that are uniquely adapted to address the symptoms of dry eye that exist today. In particular, there is a need for an improved formulation that promotes greater moisture retention by the cornea and provides an enhanced lubricating effect. There is also a need for a solution that is particularly well-suited to meet the needs of patients who are experiencing one or more dry eye symptoms as a result of computer eye strain or surgical procedures involving the cornea, particularly LASIK surgery. (The term "LASIK" is an acronym for a refractive surgical procedure known as "laser in situ keratomileusis".) Finally, there is a need for improved artificial tear formulations that contain very low concentrations of antimicrobial preservatives, so as to reduce the potential for ocular irritation caused by the preservatives. The present invention is directed to filling these needs.

SUMMARY OF THE INVENTION

The present invention is directed to the provision of unique artificial tear compositions having improved properties, relative to the prior artificial tear formulations mentioned above, as well as other formulations. The invention is also directed to methods of alleviating the symptoms of dry eye by applying the compositions of the present invention topically to the affected eyes.

The artificial tear compositions of the present invention contain a unique combination of three demulcents and an ophthalmically acceptable vehicle for the demulcents. The compositions preferably also contain electrolytes to simulate the salt content of the natural tear fluid. The compositions may also contain a nonionic surfactant to lower the surface tension of the compositions and enhance the spreading of the compositions over the surface of the cornea.

The compositions preferably also contain a unique combination of formulation components that enhance the antimicrobial activity of the compositions. This enhancement of antimicrobial activity makes it possible to reduce the amount of antimicrobial preservative (e.g., polyquaternium-1) required to satisfy preservative efficacy requirements for multi-dose ophthalmic pharmaceutical products. The formulation components utilized to enhance antimicrobial activity will include one or more of the following: (i) a borate/polyol complex, and (ii) a low molecular weight amino acid.

The compositions of the present invention are effective in providing relief from burning and irritation caused by dryness of the eyes and discomfort caused by irritation of the eyes. The compositions may also be utilized as ocular moisture drops or ocular lubricants.

DETAILED DESCRIPTION OF THE INVENTION

The artificial tear compositions of the present invention are preferably formulated as sterile, isotonic solutions. The solutions contain a combination of three demulcents: (1) hydroxypropyl methylcellulose ("HPMC"); (2) glycerin; and (3) one or more dextrans, preferably Dextran 70. The total concentration of this demulcent system in the solutions is from about 0.5 to about 5 weight/volume percent ("w/v %").

In the preferred embodiment of the present invention, the concentration of HPMC is in the range of 0.2 to 2.5 w/v %, the concentration of glycerin is in the range of 0.2 to 1 w/v %, and the concentration of dextran, in the form of Dextran 70, is 0.1 w/v %.

The artificial tear solutions of the present invention will preferably also contain one or more electrolytes to simulate the composition of natural tear fluid. As will be appreciated by those skilled in the art, the natural tear fluid contains several different ions, including potassium, calcium, magnesium and zinc. The presence of these ions in the natural tear fluid and the respective concentrations of these ions is further described in U.S. Pat. No. 5,403,598 (Beck, et al.), the entire contents of which are hereby incorporated in the present specification by reference. The role that these ions play in maintaining the function of corneal tissues is also discussed in the Beck, et al. '598 patent.

The electrolytes utilized in the compositions of the present invention will comprise one or more of the following: potassium at a concentration of between about 11 and about 25 millimoles per liter ("mmol/l"); calcium at a concentration of between about 0.2 and about 0.5 mmol/l; magnesium at a concentration of between about 0.15 and about 0.45 mmol/l; and bicarbonate at a concentration of between about 1 and about 36 mmol/l, preferably between about 6 and about 24 mmol/l. The compositions may additionally contain zinc at a concentration between about 0.005 and about 0.015 mmol/l.

The artificial tear solutions of the present invention may also contain one or more nonionic surfactants to lower the surface tension of the solutions and thereby enhance spreading of the solutions over the surface of the cornea. The preferred nonionic surfactants have an HLB value of 15 or greater. Examples of suitable nonionic surfactants include the polysorbates, such as polysorbate 80, which is also known as "Tween 80", and tetrafunctional block copolymers derived from the addition of ethylene oxide and propylene oxide to ethylenediamine. Such block polymers are commercially available from BASF Corporation under the trade name "TETRONIC™", and are also commonly identified as "poloxamines". The most preferred nonionic surfactant of this type is poloxamine 1107, which has an HLB value of 24 and an average molecular weight of 15,000. Additional examples of suitable nonionic surfactants include Tween 20, Brij 78 and Brij 700.

The artificial tear solutions of the present invention will contain one or more of the above-described nonionic surfactants in an amount sufficient to reduce the surface tension of the solutions and enhance the ability of the solutions to spread over the surface of the cornea. Such an amount is referred to herein as "an effective amount". The amount of surfactant utilized will be an amount sufficient to provide the solutions with a surface tension of from about 38 to about 45 dynes per centimeter ("dynes/cm"), which corresponds to the surface tension of human tears. The amount of surfactant required for this purpose will vary somewhat depending on the particular surfactant selected, but the surfactant concentration will generally be in the range of from 0.001 to 0.1 w/v %, and preferably 0.003 to 0.05 w/v %.

The artificial tear compositions of the present invention may be packaged as either a single dose product or a multi-dose product. The single dose product is sterile prior to opening of the package and all of the composition in the package is intended to be consumed in a single application to one or both eyes of a patient. The use of an antimicrobial preservative to maintain the sterility of the composition after the package is opened is therefore unnecessary.

Multi-dose products are also sterile prior to opening of the package. However, because the container for the composition may be opened many times before all of the composition in the container is consumed, the multi-dose products must have sufficient antimicrobial activity to ensure that the compositions will not become contaminated by microbes as a result of the repeated opening and handling of the container. The level of antimicrobial activity required for this purpose is well known to those skilled in the art, and is specified in official publications, such as the United States Pharmacopoeia ("USP") and corresponding publications in other countries. Detailed descriptions of the specifications for preservation of ophthalmic pharmaceutical products against microbial contamination and the procedures for evaluating the preservative efficacy of specific formulations are provided in those publications. In the United States, preservative efficacy standards are generally referred to as the "USP PET" requirements. (The acronym "PET" stands for "preservative efficacy testing".)

The use of a single dose packaging arrangement eliminates the need for an antimicrobial preservative in the compositions, which is a significant advantage from a medical perspective, because conventional antimicrobial agents utilized to preserve ophthalmic compositions (e.g., benzalkonium chloride) may cause ocular irritation, particularly in patients suffering from dry eye conditions or pre-existing ocular irritation. However, the single dose packaging arrangements currently available, such as small volume plastic vials prepared by means of a process known as "form, fill and seal", have several disadvantages for manufacturers and consumers. The principal disadvantages of the single dose packaging systems are the much larger quantities of packaging materials required, which is both wasteful and costly, and the inconvenience for the consumer. Also, there is a risk that consumers will not discard the single dose containers following application of one or two drops to the eyes, as they are instructed to do, but instead will save the opened container and any composition remaining therein for later use. This improper use of single dose products creates a risk of microbial contamination of the single dose product and an associated risk of ocular infection if a contaminated composition is applied to the eyes.

In view of the foregoing considerations, the ideal product is a multi-dose product that either does not contain a conventional antimicrobial preservative or contains a very low concentration of preservative. The compositions of the present invention are formulated so as to achieve these objectives.

The artificial tear solutions of the present invention that are formulated as multi-dose solutions may also contain an antimicrobial agent to prevent microbial contamination of the solution. This agent is referred to herein as "an antimicrobial preservative". The artificial tear solutions of the present invention may contain one or more antimicrobial preservatives in an amount effective to prevent microbial contamination of the solutions (referred to herein as "an antimicrobial effective amount"). The solution will preferably contain one or more antimicrobial agents in an amount sufficient to meet or exceed the PET requirements of the USP. The preferred antimicrobial preservative is polyquaternium-1, in an amount of from about 0.00001 to about 0.001 w/v %, which corresponds to a range of from about 0.1 to 10 parts per million ("ppm"), but preferably less than 0.001 w/v % (10 ppm). The most preferred concentration is 0.0001 w/v % (1 ppm) or less.

As indicated above, it has been discovered that the use of a unique combination of formulation components makes it possible to satisfy preservative efficacy requirements with very low concentrations of polyquaternium-1, such as 0.0001 w/v % or less. The ability to utilize these lower concentrations of antimicrobial preservatives is quite significant, since it is highly desirable to reduce the concentration of antimicrobial preservatives in artificial tear products. The "unique combination of formulation components" referred to above may include one or more of the following components: (i) a borate/polyol complex, or (ii) a low molecular weight amino acid. As described in the following paragraphs, these components enhance the antimicrobial activity of the solution.

The artificial tear solutions of the present invention preferably contain a water soluble borate/polyol complex to enhance the antimicrobial activity of the solutions. The use of borate/polyol complexes for this purpose is described in U.S. Pat. No. 6,143,799 (Chowhan, et al.), the entire contents of which are hereby incorporated in the present specification by reference. As indicated in the Chowhan, et al. '799 patent, the total concentration of the borate/polyol complex is in the range of 0.5 to 6.0 weight percent ("wt. %"), preferably 1.0 to 2.5 wt. %, and the molar ratio of borate to polyol is in the range of 1:0.1 to 1:10, preferably 1:0.25 to 1:2.5.

As used herein, the term "borate" shall refer to boric acid, salts of boric acid and other pharmaceutically acceptable borates, or combinations thereof. Most suitable are: boric acid, sodium borate, potassium borate, calcium borate, magnesium borate, manganese borate, and other such borate salts.

As used herein, and unless otherwise indicated, the term "polyol" shall refer to any compound having at least two adjacent —OH groups which are not in trans configuration relative to each other. The polyols can be linear or circular, substituted or unsubstituted, or mixtures thereof, so long as the resultant complex is water-soluble and pharmaceutically acceptable. Such compounds include sugars, sugar alcohols, sugar acids and uronic acids. Preferred polyols are sugars, sugar alcohols and sugar acids, including, but not limited to: mannitol, glycerin (glycerol), propylene glycol and sorbitol. Especially preferred polyols are mannitol, sorbitol, propylene glycol and glycerol; the most preferred polyol is glycerol. Combinations of polyols such as glycerol/sorbitol and glycerol/propylene glycol are also preferred.

In the artificial tear solutions of the present invention that contain glycerol, the glycerol may function as both a demulcent and as the polyol component of the borate/polyol complex.

The artificial tear solutions of the present invention may also contain a low molecular weight amino acid to enhance the antimicrobial activity of the solutions, and thereby allow a lower concentration of the antimicrobial preservative to be utilized. The use of low molecular weight amino acids to enhance the antimicrobial activity of the ophthalmic compositions is described in U.S. Pat. No. 5,741,817 (Chowhan, et al.), the entire contents of which are hereby incorporated in the present specification by reference.

The artificial tear solutions of the present invention may contain one or more amino acids in an amount of from about 0.01 to about 2.5 w/v %, more preferably an amount of from about 0.1 to about 1.0 w/v %. The low molecular weight amino acids will have a molecular weight in the range of from about 75 to about 250; the most preferred low molecular weight amino acid is glycine.

The artificial tear solutions of the present invention are formulated so as to have a pH and osmolality that are compatible with the eye. The solutions will typically have a pH in the range of from about 6.8 to about 7.8, and an osmolality of from about 250 to about 350 milliosmoles/kilogram water ("mOsm/kg").

The artificial tear solutions of the present invention may be formulated to have an enhanced viscosity, so as to increase the retention time of the solutions in the eye and/or increase the comfort or cushioning effect experienced by the patient when the solutions are applied to the eye. The viscosity of the solutions will generally be in the range of from about 1 to about 20 centipoise ("cps"), preferably from about 2 to about 20 cps, and most preferably from about 5 to 20 cps.

The artificial tear solutions of the present invention may be applied topically to the cornea to relieve dry eye symptoms attributable to various causes. The solutions may also be utilized as ocular moisture drops or ocular lubricants, and as ocular comfort drops. The solutions will typically be applied by placing one to two drops either on the cornea or in the cul de sac of the eye. The solutions are primarily intended for use in humans, but may also be utilized in other mammals.

As a result of the very mild preservative system employed in the solutions of the present invention, it is possible to apply the solutions to the eyes several times per day without risk of irritating ocular tissues or causing other unwanted side effects. It is therefore possible to utilize the solutions for purposes of tear replacement and ocular lubrication in patients whose corneas have become irritated due to lack of adequate hydration, physical or chemical irritants, or medical procedures. The solutions of the present invention are particularly useful in alleviating dry eye symptoms associated with LASIK surgery, photorefractive keratectomy ("PRK"), laser thermal keratoplasty ("LTK"), and similar procedures involving either the ablation of corneal tissues by means of lasers, or other physical manipulations or modifications of those tissues.

The following examples describe certain preferred embodiments of the present invention:

EXAMPLE 1

| Ingredient | Amount (w/v %) |
|---|---|
| Hydroxypropyl Methylcellulose (2910) (E4M) | 0.3 |
| Dextran 70 | 0.1 |
| Polysorbate 80 (Tween 80) | 0.005 |
| Sodium Chloride | 0.4 |
| Boric Acid | 0.8 |
| Glycine | 0.1 |
| Potassium Chloride | 0.038 |
| Calcium Chloride (Dihydrate) | 0.0053 |
| Magnesium Chloride (Hexahydrate) | 0.0065 |
| Zinc Chloride | 0.00015 |
| Glycerin | 0.2 |
| Polyquaternium-1 | 0.001 + 5% excess |
| NaOH/HCl | q.s. pH 7.4 |
| Purified Water | q.s. to 100 |
| Physical and Optical Parameters | |
| pH | 7.4 |
| Osmolality (mOsm/kg) | 306 |
| Refractive Index | 1.3341 |
| Surface Tension | 40.8 |
| Viscosity (cps) | 7.0 |

The foregoing solution was prepared by means of the procedures described below:

I. Preparation of a Sterile Receiving Vessel

Prepare a sterile receiving vessel with sterile filtration assembly attached and calibrate the compounding vessel. Calibrate the compounding vessel to 100% of the final volume with purified water.

II. Preparation of 2% HPMC Stock Solution

1. Weigh out HPMC powder.
2. Heat purified water (50% of batch volume) to boil. Stop heating.
3. While stirring with a high-speed propeller mixer, add the HPMC powder slowly until it is uniformly dispersed.
4. Add cold purified water to 100% of batch volume.
5. Place the container in a refrigerator overnight.
6. Filter the HPMC stock solution through a 15 μm-polish filter and collect the filtered 2% HPMC solution in a clean container.
7. Label and store the solution in refrigerator for further use.

III. Compounding Steps

1. Place the required amount of 2% HPMC stock solution in the sterile receiving vessel ("Container I") and autoclave the vessel at 121° C. for 35 minutes.
2. Remove the vessel from autoclave. Allow stirring while cooling down to room temperature.
3. In another clean receiving vessel ("Container II"), add purified water (20–30° C.) up to 50% of the final batch volume.

4. Weigh and add the following ingredients to Container II:
   a. sodium chloride
   b. boric acid
   c. potassium chloride
   d. calcium chloride
   e. magnesium chloride
   f. zinc chloride
   g. glycine
   h. dextran 70
   i. polysorbate 80
   j. glycerine.
   k. polyquaternium-1.
   With continuous stirring, dissolve the above chemicals until the solution is clear.
5. Measure the pH of the salt solution in Container II. If necessary, adjust pH to 7.2 using 6N sodium hydroxide and/or 6N hydrochloric acid.
6. Filter the salt solution in Container II through a 0.22 micron Millipore sterilizing filter(s) into the receiving vessel (Container I).
7. Adust to 100% of final volume with purified water (20–30° C.) and measure the final pH aseptically.

EXAMPLE 2

It has been determined that the concentration of polyquaternium-1 in the solution of Example 1 can be further reduced. A solution identical to the solution of Example 1, but containing polyquaternium-1 at a concentration of only 0.0001 w/v % (i.e., one-tenth of the amount utilized in the solution of Example 1), was prepared and found to have the following properties:

| Physical and Optical Parameters | |
| --- | --- |
| pH | 7.40 |
| Osmolality | 307 |
| Refractive Index | 1.3334 |
| Surface tension | 41.1 |
| Viscosity (cps) | 6.4 |

EXAMPLE 3

The solution of Example 1 was tested to determine if the solution satisfies the USP PET requirements. The solution was tested in accordance with the procedures described in the United States Pharmacopoeia $24^{th}$ Edition (2000), Section 51, pages 1809–1811. It was determined that the solution exhibits levels of antimicrobial activity against the test microorganisms that exceeds the levels required by the USP PET standards. The test results, expressed as log order reductions in initial populations of microorganisms, were as follows:

| Microorganism | Time (days) | Lot 1 | Lot 2 | Lot 3 |
| --- | --- | --- | --- | --- |
| Staphylococcus aureus | | $(8.6 \times 10^5)$ | $(1.3 \times 10^6)$ | $(8.6 \times 10^5)$ |
| | 7 | 4.9 | 5.1 | 4.9 |
| | 14 | 4.9 | 5.1 | 4.9 |
| | 28 | 4.9 | 5.1 | 4.9 |
| Pseudomonas aeruginosa | | $(7.9 \times 10^5)$ | $(5.6 \times 10^5)$ | $(8.6 \times 10^5)$ |
| | 7 | 4.9 | 4.7 | 4.9 |
| | 14 | 4.9 | 4.7 | 4.9 |
| | 28 | 4.9 | 4.7 | 4.9 |
| Escheria coli | | $(7.5 \times 10^5)$ | $(1.3 \times 10^6)$ | $(8.2 \times 10^5)$ |
| | 7 | 4.9 | 5.1 | 4.9 |
| | 14 | 4.9 | 5.1 | 4.9 |
| | 28 | 4.9 | 5.1 | 4.9 |
| Candida albicans | | $(8.0 \times 10^5)$ | $(6.4 \times 10^5)$ | $(5.5 \times 10^5)$ |
| | 7 | 4.9 | 4.8 | 4.7 |
| | 14 | 4.9 | 4.8 | 4.7 |
| | 28 | 4.9 | 4.8 | 4.7 |
| Aspergillus niger | | $(2.1 \times 10^6)$ | $(1.2 \times 10^6)$ | $(1.6 \times 10^6)$ |
| | 7 | 1.9 | 1.8 | 1.8 |
| | 14 | 2.0 | 2.0 | 1.6 |
| | 28 | 2.1 | 2.0 | 2.8 |

Three lots of the solution of Example 1 were tested (i.e., Lots 1–3). The numbers in parentheses above are the initial inoculum levels. The numbers below the inoculum levels represent the log order reductions in the microorganism populations at specified time points.

EXAMPLE 4

The solutions of Example 2 was tested to determine if the solution satisfies the USP PET requirements. The USP procedures referred to in Example 3 above were utilized. It was determined that the solution exhibits levels of antimicrobial activity against the test microorganisms that exceed the levels required by the USP PET standards. The test results, expressed as log order reductions in initial populations of microorganisms, were as follows:

| Microorganism | Time (days) | Lot 1 | Lot 2 | Lot 3 |
| --- | --- | --- | --- | --- |
| Staphylococcus aureus | | $(5.6 \times 10^5)$ | | |
| | 7 | 4.7 | 4.8 | 4.8 |
| | 14 | 4.7 | 4.8 | 4.8 |
| | 28 | 4.7 | 4.8 | 4.8 |
| Pseudomonas aeruginosa | | $(6.6 \times 10^5)$ | | |
| | 7 | 4.8 | 4.9 | 5.0 |
| | 14 | 4.8 | 4.9 | 5.0 |
| | 28 | 4.8 | 4.9 | 5.0 |
| Escheria coli | | $(8.2 \times 10^5)$ | | |
| | 7 | 4.9 | 4.9 | 4.9 |
| | 14 | 4.9 | 4.9 | 4.9 |
| | 28 | 4.9 | 4.9 | 4.9 |
| Candida albicans | | $(9.2 \times 10^5)$ | | |
| | 7 | 2.6 | 2.5 | 2.4 |
| | 14 | 5.0 | 4.5 | 4.4 |
| | 28 | 5.0 | 4.9 | 4.9 |
| Aspergillus niger | | $(1.3 \times 10^6)$ | | |
| | 7 | 1.7 | 1.1 | 1.1 |
| | 14 | 1.6 | 1.1 | 1.0 |
| | 28 | 1.6 | 1.6 | 1.8 |

Three lots of the solution of Example 2 were tested (i.e., Lots 1–3). The inoculum levels utilized in the testing of Lot 1 of the solution are set forth in parentheses above. Similar inoculum levels were utilized in the testing of Lots 2 and 3 of the solution.

Solutions containing concentrations of polyquaternium-1 of 0.00003 w/v % (0.3 ppm) and 0.00005 w/v % (0.5 ppm) have also been tested and found to have antimicrobial activity levels similar to the solutions of Examples 1 and 2 above, which contained polyquaternium-1 concentrations of 0.001 w/v % (10 ppm) and 0.0001 w/v % (1 ppm), respectively. These additional solutions were identical to the solutions of Examples 1 and 2, except for the concentration of polyquaternium-1 utilized.

We claim:

1. An improved artificial tear solution for alleviating dry eye symptoms said solution having the following formula:

| Ingredient | Amount (w/v %) |
| --- | --- |
| Hydroxypropyl Methylcellulose (2910) (E4M) | 0.3 |
| Dextran 70 | 0.1 |
| Polysorbate 80 (Tween 80) | 0.005 |
| Sodium Chloride | 0.4 |
| Boric Acid | 0.8 |
| Glycine | 0.1 |
| Potassium Chloride | 0.038 |
| Calcium Chloride (Dihydrate) | 0.0053 |
| Magnesium Chloride (Hexahydrate) | 0.0065 |
| Zinc Chloride | 0.00015 |
| Glycerin | 0.2 |
| Polyquaternium-1 | 0.00001–0.001 |
| NaOH/HCl | q.s. pH 7.4 |
| Purified Water | q.s. to 100. |

2. An improved artificial tear solution according to claim 1, wherein the concentration of polyquaternium-1 is 0.001%.

3. An improved artificial tear solution according to claim 1, wherein the concentration of polyquaternium-1 is less than 0.001 w/v%.

4. An improved artificial tear solution according to claim 3, wherein the concentration of polyquaternium-1 is 0.00001 to 0.0001 w/v%.

5. An improved artificial tear solution according to claim 3, wherein the concentration of polyquaternium-1 is 0.0001 w/v%.

* * * * *